United States Patent [19]
Anderson

[11] Patent Number: 5,782,825
[45] Date of Patent: Jul. 21, 1998

[54] MICROLENS TIP ASSEMBLY FOR LIGHT DELIVERY CATHETER

[75] Inventor: Steven C. Anderson, Santa Barbara, Calif.

[73] Assignee: Miravant Systems, Inc., Santa Barbara, Calif.

[21] Appl. No.: 611,592

[22] Filed: Mar. 7, 1996

[51] Int. Cl.$^6$ .................................. A61B 17/39
[52] U.S. Cl. .................................. 606/15; 606/16
[58] Field of Search .................................. 606/7, 13, 1, 17; 385/31, 33, 35, 78–81

[56] References Cited

U.S. PATENT DOCUMENTS

| | | | |
|---|---|---|---|
| 4,273,109 | 6/1981 | Enderby | 606/16 |
| 5,163,935 | 11/1992 | Black et al. | 606/17 |
| 5,190,536 | 3/1993 | Wood et al. | 606/16 |
| 5,231,684 | 7/1993 | Narciso, Jr. et al. | 385/80 |
| 5,403,308 | 4/1995 | Wood et al. | 606/17 |
| 5,486,171 | 1/1996 | Chou | 606/16 |
| 5,514,125 | 5/1996 | Lasser et al. | 606/16 |

*Primary Examiner*—Michael Peffley
*Attorney, Agent, or Firm*—Michael G. Petit

[57] ABSTRACT

A microlens tip assembly for focusing output light from a light delivery catheter upon a target tissue. Due to the inherent divergence of output light from diode lasers, when such divergent light is conducted from the proximal end of a catheter to the distal end by means of a fiber optic, a portion is reflected at the fiber/air/lens interface to impinge upon the microlens housing area thereby heating the housing assembly resulting in overheating at high power levels and possible device failure and/or tissue damage. The present high-powered microlens includes a rear and front mount, both of which are fabricated from a non-light-absorbing material such as transparent or white plastic. The use of transparent or non-ligh-absorbing plastic components decreases the amount of heating of the tip assembly during light delivery, thereby solving the problem of therapeutic light delivery device failures and/or tissue damage due to overheating.

3 Claims, 2 Drawing Sheets

5,782,825

1

MICROLENS TIP ASSEMBLY FOR LIGHT DELIVERY CATHETER

BACKGROUND OF THE INVENTION

1. Field of the Invention

This invention relates to a high-power light delivery catheter and more particularly to a forward illuminating invasive light delivery catheter having light output focusing means thereon.

2. Prior Art

Invasive light delivery catheters are well known in the art. For example, U.S. Pat. No. 5,231,684 (hereinafter referred to as '684) to Narciso, Jr. et al. discloses a fiber optic catheter having a microlens on the distal end thereof which distal end is adapted for insertion into the body of a patient thereafter to illuminate a tissue adjacent thereto. The microlens at the terminus of the catheter is held in position and spaced from the distal, invasive end of the fiber optic by means of a collet which is slideably and coaxially mounted upon an outer covering at the distal portion of the fiber optic. The collet has means on the distal end thereof to securely hold the microlens. The collet is opaque and absorbs light which is reflected from the lens, scattered from the fiber optic or otherwise is incident thereon.

Wood et al. in U.S. Pat. No. 5,190,536 (hereinafter referred to as '586) disclose a fiber optic catheter having a spherical microlens affixed to the distal portion thereof. The '586 catheter comprises a fiber optic terminated distally by a portion of the fiber optic wherein the outer cladding has been removed to expose the core. The stripped portion and an adjacent portion of the intact, clad fiber optic is bridged and enveloped by a tubular metal collet which holds a spherical or hemispherical lens distal to the distal end of the fiber optic. The distance between the spherical or hemispherical lens and the distal tip of the fiber optic may be adjusted by threaded means on the inside of the collet. As with the microlens catheter referenced above in the '684 patent, the catheter cannot handle power levels in excess of one or two watts because overheating in the collet by unwanted absorption of light causes structural failure of the microlens assembly and possible tissue damage. The divergence inherent in diode lasers causes light to be reflected into the lens housing assembly from the fiber/lens interface area thereby heating the housing assembly and resulting in possible device failure at high temperatures. Thus, it is advantageous to provide a light delivery catheter having a microlens thereon which can deliver light from a divergent light source at power levels of light in excess of one watt to a target distally thereto continuously for a period of time on the order of minutes without undue heating and failure of the distal end of the catheter.

SUMMARY OF THE INVENTION

It is a first object of this invention to provide a light delivery catheter operable for illuminating a target tissue within or on a patient wherein the catheter is capable of continuously delivering light energy to a target tissue without structural failure due to overheating of the catheter.

It is a second object of this invention to provide an improved light delivery catheter having a microlens focusing assembly thereon wherein the assembly can be inexpensively manufactured and easily adjusted to deliver focused light which will meet a variety of needs.

It is a further object of this invention to provide a microlens assembly for a fiber optic catheter wherein the assembly is useful for delivering focused light to a target positioned distal to the catheter wherein the microlens tip assembly does not absorb light to a significant extent during continual operation.

It is yet another object of the invention to provide a microlens tip assembly for a light delivery catheter which enables the catheter to deliver light from a highly divergent light source at high power levels in excess of 3 watts wherein the microlens assembly does not overheat during operation.

The features of the invention believed to be novel are set forth with particularity in the appended claims. However, the invention itself both as to organization and to method of operation, together with further object and advantages thereof may best be understood by reference to the following description taken in conjunction with the accompanying drawings in which;

DESCRIPTION OF THE PREFERRED EMBODIMENTS

Figure 1:
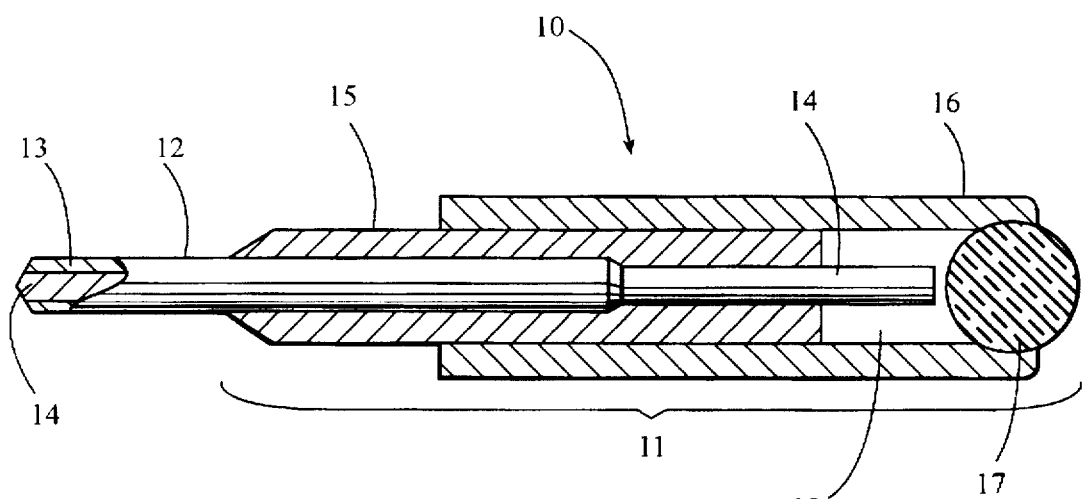
FIG. 1 is an elevational, partially cross-sectional view of a microlens tip assembly in accordance with the present invention with a spherical lens formed into the front mount.

Referring now to FIG. 1, the distal end of a light delivery catheter 10 has distal portion 11 which comprises the microlens tip assembly for the catheter. The microlens tip assembly 11 is affixed to the outer surface of a fiber optic 12 which has a portion of the cladding 13 on the distal end thereof removed to expose the core 14. A rear mount assembly 15 comprising a non-light-absorbing material, preferably a transparent polycarbonate sleeve having a low thermal conductivity, having an axial lumen machined to encase and bridge the stripped portion and an adjacent clad portion of the fiber optic 12 near the distal end of the fiber optic core 14 and matingly accommodate the fiber optic 12 therewithin is inserted over the end of the fiber. An outer front mount assembly 16 comprising an optically non-light absorbing, preferably transparent plastic tubing having a low thermal conductivity and an inner axial lumen 18 dimensioned to snugly accommodate the outer surface of the rear mount 15 therewithin and an optically clear lens 17, such as, for example, a sapphire or quartz ball lens, affixed, preferably by thermal forming to occlude the distal portion thereof, is slid over the rear mount assembly 15 to position the optical ball lens 17 adjacent the distal tip of the fiber optic core 14. The distance between the optical ball lens 17 and the distal tip of the fiber optic core 14 can be adjusted by sliding the front mount assembly axially over the rear mount assembly to position the distal end of the fiber optic at the focal length of the lens or as otherwise desired. Once the desired distance is attained, the front mount assembly can be affixed to the rear mount assembly by means of a suitable adhesive such as cyanoacrylate or a UV curable resin or held in position by means of a mechanical crimp subject to certain disadvantages discussed below.

The front mount lumen 18 provides a space between the distal tip of the core 14 of the fiber optic 12 and the lens 17 which may be filled with a transparent fluid such as liquid, or a gas such as air or a solid material such as transparent, partially cured or cured silicone. The front mount portion of the microlens tip assembly is preferably made from a transparent or minimally light absorbing plastic which is extruded to form a tube having an inner lumen diameter which matingly accommodates the outer diameter of the rear mount assembly therewithin. A means for holding a lens such as, for example, a sapphire ball is machined into the distal end of the plastic extruded tubing and a lens inserted therewithin and thermally affixed thereto to occlude the lumen 18. The front mount may then be slid over the rear mount and adjusted. The front-and-rear mount may be fixed into position and the entire assembly placed on the catheter.

Figure 2:
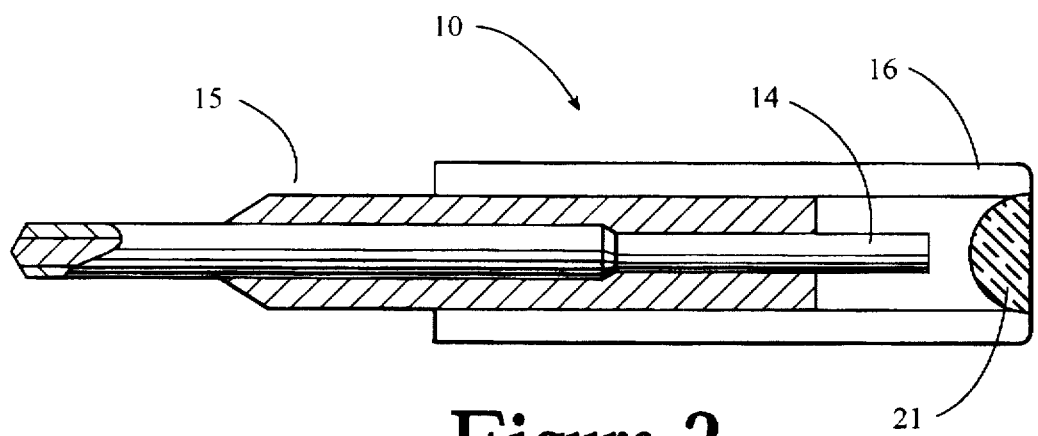
FIG. 2 is an elevational, partially cross-sectional view of a microlens assembly mounted on the distal end of a fiber illustrating a plan-convex hens mounted to present a blunt distal tip.
Figure 3:
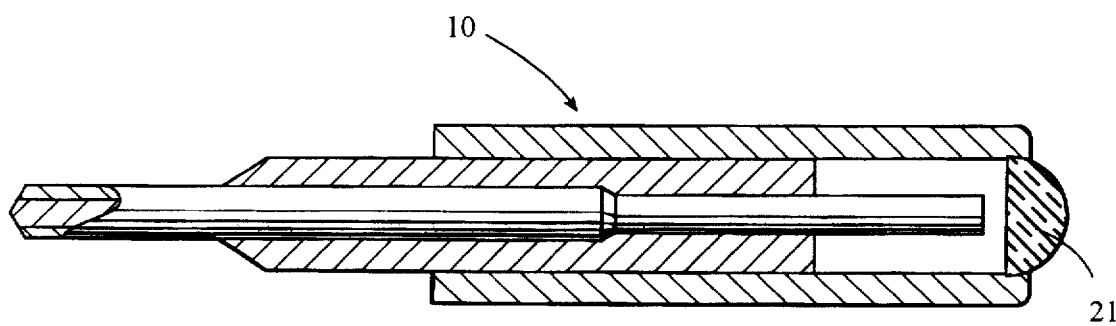
FIG. 3 is an elevational, partially cross-sectional view of a microlens assembly mounted on the distal end of a fiber illustrating a plan-convex hens mounted to present a rounded distal tip.
Figure 4:
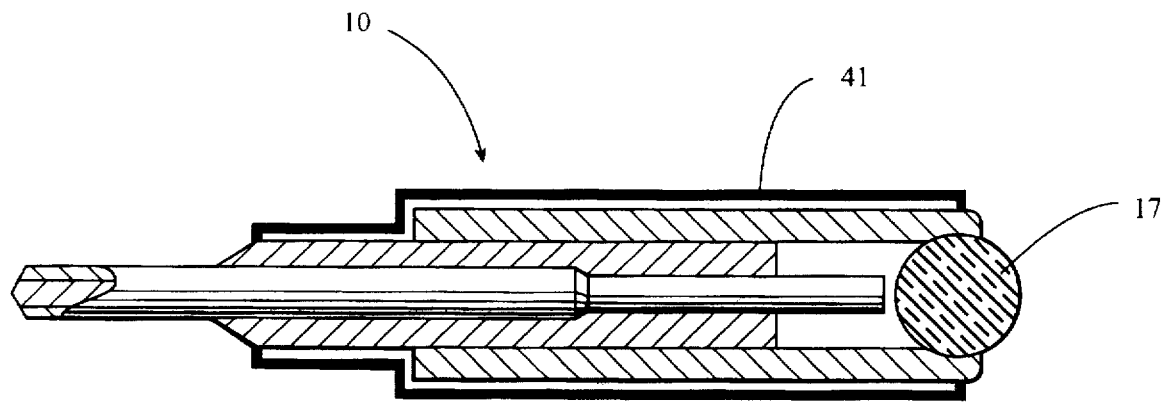
FIG. 4 is an elevational, partially cross-sectional view of the microlens assembly enclosed in an opaque outer sheath.
Figure 5:
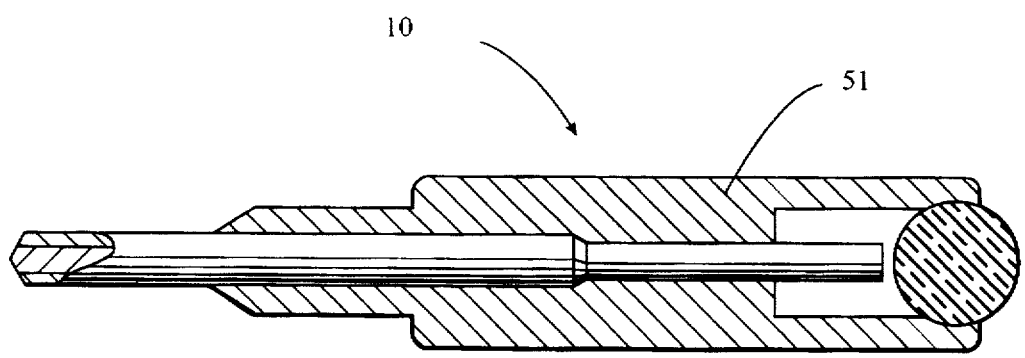
FIG. 5 is an elevational. Partially cross-sectional view of the microlens assembly wherein the front and rear mounts form a unitary structure.

Various embodiments of the microlens tip assembly are possible employing various lenses. FIG. 2 illustrates the microlens tip assembly with a hemispherical lens 21 mounted to present a flat distal end. FIG. 3 illustrates the microlens tip assembly with a hemispherical lens mounted in the front mount to present a rounded tip. FIG. 4 shows the device with an opaque sheath 41 attached to the rear mount. The sheath 41 is thermally isolated from the front mount to avoid heating. The sheath 41 may be used in applications where the side light output must be blocked (e.g. in a body cavity as opposed to a skin surface application). FIG. 5 shows the microlens assembly with the front and rear mounts combined into a unitary lens mount 51. The unitary lens mount 51 may be formed by injection molding. The unitary lens mount 51 can incorporate any of the lens configurations shown in FIGS. 1, 2 and 3.

The rear mount assembly 15 can either be machined or injection molded. The rear mount is bonded by adhesive means, such as, for example, cyanoacrylate, or a UV cured resin, directly to the fluoropolymer jacket (buffer) of the fiber optic after the buffer has been chemically etched. A suitable etchant is Tetra-etch® (W. L. Gore & Associates, Inc., P.O. Box 3000 Flagstaff, Ariz. 86003-9981). An adhesive bond eliminates the need to mechanically crimp a mount sleeve onto the buffer. The crimp process can lead to damage to the fiber optic cladding, and thus added light loss into the lens housing assembly.

The front mount assembly consists of a lens which is thermally formed into clear, preferably plastic tubing. This construction eliminates the need for use of epoxy near the lens. During high powered operation, any epoxy which is near the lens or the fiber/lens interface can be vaporized. This effect can lead to decreased performance and possible failure of the system.

While particular embodiments of the present invention have been illustrated and described, it would be obvious to those skilled in the art that various other changes and modifications can be made without parting from the spirit and scope of the invention. For example, the rear mount and front mount may be of unitary construction, the inner diameter machined to accommodate the bridging function to strengthen the stripped core and the distal end having an inner diameter dimensioned to accommodate a lens therewithin. It is therefore intended to cover in the appended claims all such changes and modifications that are within the scope of this invention.

What I claim is:

1. A light delivery catheter having a length wherein the light delivery catheter comprises a fiber optic having a cylindrical light-conducting core coextensive with the length thereof, said catheter having a proximal end adapted to receive light from a source of light and a distal end and a first outer diameter, at least a portion of said core having cladding thereon presenting a second outer diameter, and a microlens affixed to the distal end of said light delivery catheter, the microlens comprising:

(a) a rear mount comprising a transparent cylindrical tubing having a length, an outer diameter, a proximal portion, a distal portion and a cylindrical inner lumen coextensive with the length thereof, said proximal portion of said cylindrical inner lumen having an inner lumen diameter greater than or equal to said second outer diameter of said cladding of said fiber optic and the distal portion of said inner lumen having an inner lumen diameter equal to or greater than said first outer diameter of said core; and (b) a front mount comprising a transparent cylindrical tubing having an axial cylindrical lumen therewithin and being constructed of a material which is a poor thermal conductor wherein the diameter of said axial cylindrical lumen is dimensioned to snugly accommodate said outer diameter of said rear mount therewithin, said front mount being mounted on said distal end of said rear mount and telescopically movable thereupon, and wherein said distal end has an axially symmetric circular aperture formed therethrough; and (c) a spherical light transparent lens rigidly affixed within said circular aperture disposed within the distal end of said front mount and axially symmetric with respect to said cylindrical lumen; and (d) an opaque sheath affixed to and enveloping at least the distal end of the rear mount.

2. The microlens tip assembly of claim 1 wherein said front mount is optically transparent.

3. The light delivery catheter of claim 1, wherein said opaque sheath has a reflective inner surface.

\* \* \* \* \*